United States Patent [19]

Chavdarian et al.

[11] 4,321,387
[45] Mar. 23, 1982

[54] PROCESS FOR THE PREPARATION OF OPTICALLY ACTIVE NICOTINE ANALOGS

[75] Inventors: Charles G. Chavdarian; Edward B. Sanders, both of Richmond, Va.

[73] Assignee: Philip Morris, Incorporated, New York, N.Y.

[21] Appl. No.: 132,558

[22] Filed: Mar. 21, 1980

[51] Int. Cl.³ .................. C07D 401/04; C07D 207/12
[52] U.S. Cl. .................... 546/281; 546/282; 260/326.5 R; 424/264
[58] Field of Search .............. 546/281, 282; 260/326.5 R

[56] References Cited

U.S. PATENT DOCUMENTS

| 2,695,301 | 11/1954 | Blicke | 260/326.3 |
| 2,890,222 | 6/1959 | Omietanski | 546/281 |
| 3,247,213 | 4/1966 | Buchel et al. | 546/193 |
| 4,155,909 | 5/1979 | Sanders et al. | 546/282 X |

FOREIGN PATENT DOCUMENTS 820503 9/1959 United Kingdom .

OTHER PUBLICATIONS

Haglid; Acta Chemica Scandinavica, 21(1967), pp. 329–334.
Sanders, et al.; J. Org. Chem., 43(1978), pp. 324–330.
Catka, et al.; J. Org. Chem., 43(1978), pp. 2125–2127.
Noller, "Chemistry of Organic Compounds," 1965, 3rd ed., pp. 363–366.
Yamamoto, et al.; Agr. Biol. Chem., 26, (1962), pp. 709–716.
Yamamoto, et al.; Agr. Biol. Chem., 27, (1963), pp. 445–449.
Kamimura, et al.; Agr. Biol. Chem., 27, (1963), pp. 450–453, 684–688.
Soeda, et al.; Agr. Biol. Chem., 32, (1968), pp. 568–573, 747–752.
Yamamoto, et al.; Agr. Biol. Chem., 32, (1968), pp. 1341–1348.
C. A., 30:8502–8503, (1936), Richardson, et al.
C. A., 35:266, (1941), Hansberry et al.
Bowman, et al., Biochem. Prep., 10, (1963), pp. 36–39.
Sanders, et al.; J. Org. Chem., 40, (1975), pp. 2848–2849.
Blicke, et al.; J.A.C.S., 77, (1955), pp. 29–31.
Renshaw, et al.; 61, J.A.C.S., (1939), pp. 1195–1198.
Brain, et al.; J. Chem. Soc., (1961), pp. 633–639.
Ikegami, et al.; Tetrahedron, 30, (1974), pp. 2077–2086.
Paul, et al.; Bull. Soc. Chim. France, (1958), pp. 736–741.
Bryson, et al.; J. Org. Chem., 39, (1974), pp. 3436–3438.
Karrer, et al.; Helv. Chim. Acta., 31, (1948), pp. 1617–1623.

Primary Examiner—Joseph Paul Brust
Attorney, Agent, or Firm—Arthur I. Palmer, Jr.; George E. Inskeep

[57] ABSTRACT

A method is disclosed for preparing chiral nicotine and nicotine analogues of the formula:

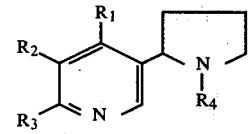

wherein $R_1$, $R_2$, and $R_3$ are hydrogen or alkyl and $R_4$ is alkyl. Also disclosed are novel intermediate compounds and a novel method for preparing 1-methylprolinol from prolinol, which compounds and method are useful for the preparation of these nicotinoids.

28 Claims, No Drawings

PROCESS FOR THE PREPARATION OF OPTICALLY ACTIVE NICOTINE ANALOGS

BACKGROUND OF THE INVENTION

1. Field of the Invention

The present invention relates to a novel process for the preparation of enantiomerically pure nicotine analogs containing alkyl substituents on the pyridine ring at the 4, 5, and/or 6 positions. The invention also relates to intermediate compounds useful for the preparation of such nicotine analogs which analogs are useful as insecticides.

2. Description of the Prior Art

Nicotine has been used as an insecticide for many years. Yamamoto has studied a number of nicotinoids (both natural and synthetic) with regard to their insecticidal activity [*Agr. Biol. Chem.*, 26, 709 (1962); Id., 27, 445 (1963); Id., 27, 450 (1963), Id., 27, 684 (1963); Id., 32, 568 (1968); Id., 32, 747 (1968); Id., 32, 1341 (1968)]. Several of the analogs studied possessed significant toxicity towards aphids, house flies, and cockroaches. Individual enantiomers of nicotinoids have been shown to display wide differences in insecticidal activity [Richardson, C., Craig, L., and Hansberry, R., *J. Econ. Entomol.*, 29, 850 (1936); Hansberry, R., and Norton, L., Id., 33, 734 (1940)]. For example, d-nicotine was found to be five times less effective against aphids then when natural l-nicotine. Further differences in insectidal activity between individual enantiomers and their racemic mixtures were demonstrated: the racemic mixture, d, l-nicotine, was half as potent against aphids as l-nicotine and the racemic mixture, d, l-nornicotine, was less potent against aphids than either of its enantiomeric components although the individual d- and l-nornicotine enantiomers possessed comparable toxicity against aphids. Clearly, the optical activity of a given nicotinoid is important to its biological properties and methods for the production of nicotinoids having specific optical activity are of considerable interest.

McKennis has prepared (S)-cotinine, a nicotine analogue and metabolite from (S)-nicotine [Bowman, E. R., and McKennis, H. Jr., *Biochem. Prep.*, 10, 36 (1963)]. Sanders prepared a mixture of (2'S)-cis-and-trans-5'-cyanonicotine from (S)-cotinine using the method of McKennis for the preparation of the (S)-cotinine [Sanders, E. B., DeBardeleben, J. F., and Osdene, T. S., *J. Org. Chem.*, 40, 2848 (1975)]. Note that both McKennis and Sanders altered only the pyrrolidine ring of the nicotine skeleton.

Compare Haglid, F., *Acta. Chem. Scand.*, 21, 329 (1967) which discloses nicotine analogs containing alkyl substituents on the pyridine ring. Haglid synthesized a mixture of 6-methylnicotine and 4-methylnicotine by the addition of methyllithium to (S)-(−)-nicotine. Although both products possessed optical activity [Id., at p. 333, Table 5], they appeared to have undergone partial racemization since the unreacted nicotine recovered had undergone racemization to a degree of 67%.

All of the methods discussed above—McKennis, Sanders, and Haglid—derive optically active nicotine analogs from natural (S)-(−)-nicotine. This not only limits the flexibility of pyridine substitution (Haglid was able to produce only mixtures of 4-, 6-, and possibly 2-methylnicotine), but also restricts the scope of possible products to (S)-nicotinoids.

No direct synthesis of enantiomerically pure nicotine or nicotine analogs containing alkyl substituents on the pyridine ring exist in the literature. (In this context, the term "direct" connotes a synthesis from commercially available enantiomers wherein an enantiomerically pure product is recovered without the need for resolving a racemic or partially racemic mixture.) Because indirect synthesis of enantiomerically pure nicotine analogs are difficult and time consuming, generally requiring formation and separation (e.g., fractional crystallization) of diastereomeric salts, direct synthetic methods from commercially available compounds are highly desirable.

A preferred embodiment of the process of this invention employs commercially-available enantiomers of prolinol and the precursor enantiomers of proline as starting materials for the preparation of corresponding optically active N-substituted 2-hydroxymethylpyrrolidines. The hydroxymethyl enantiomer is converted to an optically active N-substituted 2-cyanomethylpyrrolidine via an N-substituted 2-chloromethylpyrrolidine, a pyridine-ring-forming group is added to the cyanomethylpyrrolidine, and the optically active nicotine or nicotine analog is formed by ring closure of the resulting compound and subsequent reduction.

The compound 1-methyl-2-hydroxymethylpyrrolidine (i.e., 1-methylprolinol) has been produced from a variety of starting materials, but those known starting materials do not include prolinol or optically active prolinol. U.S. Pat. No. 2,695,301 discloses a method comprising the reduction of a pyrrolidine obtained from diethyl glutamate with lithium aluminum hydride following by reaction with chloral and reduction of the N-formyl derivative thus formed with lithium aluminum hydride. Also see Blicke, F. F., and Lu, C., *J. Am. Chem. Soc.*, 77, 29 (1955). Renshaw suggests a preparation from ethyl 1-methylpyrrole-2-carboxylate by reduction with sodium and ethanol. Renshaw and Cass, *J. Am. Chem. Soc.*, 61, 1195 (1939). Both of the foregoing methods have been criticized because they require expensive starting materials or reagents for the preparation of the required product. British Pat. No. 820,503 at p. 1, lines 14–29. Soulal prepared separable mixtures of 1-alkyl-2-hydroxymethylpyrrolidines and isomeric 3-hydroxypiperidines by producing 2,5-dibromoamyl acetate from tetrahydrofurfuryl alcohol by ring opening with HBr in an alkyl carboxylic acid (e.g., acetic acid) and ring closing of the dihalogeno-amyl acetate with a primary amine followed by saponification. Id. Alkaline hydrolysis of 1-methyl-3-chloropiperidine has been found to yield 1-methyl-2-hydroxymethylpyrrolidine as the only product. Brain, E. G., Doyle, F. P., and Mehta, M. D., *J. Chem. Soc.* 633 (1961). Of the foregoing methods, only that of Blicke (U.S. Pat. No. 2,695,301) may produce an optically active product [see Brain, supra, at 634, second full paragraph.]

Quantitative conversion of racemic 1-methyl-2-hydroxymethylpyrrolidine to racemic 1-methyl-2-chloromethylpyrrolidine hydrochloride with an excess of thionyl chloride in chloroform is well known in the literature. Id. at 636; Ikegami, S., Uoji, K., and Akaboshi, S., *Tetrahedron*, 30, 2077, 2082 (1974). Similarly, replacement reactions of a racemic chloromethyl compound with a nucleophilic cyanide reagent are suggested by the literature. *Bull, Soc. Chim. France* 1958, 736, 741 (refluxed 1-ethyl-3-chloropiperidine with KCN to form 1-ethyl-2-cyanomethylpyrrolidine); Brain supra at p. 639 (refluxed 1-methyl-3-chloropiperidine with NaCN to form 1-methyl-2-cyanomethylpyrrolidine).

However, note that the replacement reactions suggested involved 1-alkyl-3-chloropiperidine and that only the corresponding 1-alkyl-2-cyanomethylpyrrolidine derivatives rather than mixtures of pyrrolidine and piperidine products resulted. Furthermore, direct displacement of a 1-alkyl-2-chloromethyl pyrrolidine has not been shown in the literature.

Regarding the ring closure of the cyanomethylpyrrolidine contemplated by the present inventors, methyl 2-bromonicotinate has been prepared from methyl 2-cyano-5-methoxy-2,4-pentadienoate with 30% HBr/acetic acid. Bryson, T. A., et al., *J. Org. Chem.*, 39, 3436 (1974). However, Bryson states that an ester moiety is important to the cyclization. Id. at 3437. Cyclization of the cyanomethylpyrrolidine derivative produced according to the process of the present invention has been successfully effected without the presence of an ester functionality.

SUMMARY OF THE INVENTION

The present invention concerns a process for the preparation of nicotine analogs, and particularly concerns a new and direct process for the preparation of enantiomerically pure compounds represented by the formula:

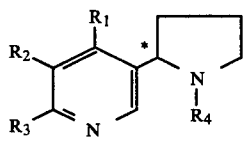

I wherein $R_1$, $R_2$, and $R_3$ are alkyl or hydrogen and $R_4$ is alkyl. Compounds of Formula I are effective insecticides.

The present invention also concerns a new and improved process for the preparation of N-substituted 2-hydroxymethylpyrrolidines which are valuable intermediates for the preparation of therapeutic substances. More particularly, this aspect of the invention is concerned with the preparation of optically active 1-alkyl-prolinols which are intermediates for the preparation of the optically active nicotine and nicotine analogs represented by Formula I.

The present invention further concerns intermediate products which are useful in the production of compounds of Formula I and are represented by the formula:

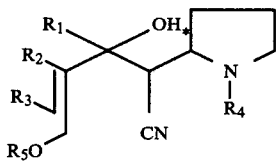

II wherein $R_1$, $R_2$, $R_3$, and $R_4$ are as described above and $R_5$ is alkyl. Preferably $R_5$ is methyl or ethyl.

The symbol "*" is used in the formulas set forth herein to designate an asymmetric (or chiral) carbon atom. "Alkyl" means straight chain or branched alkyl groups with 1 to 6 carbon atoms, for example methyl, ethyl, propyl, isopropyl, butyl and the like, with methyl being preferred.

The compounds within the scope of Formula I have two basic nitrogen atoms and can therefore form acid addition salts with inorganic and organic acids: for example, hydrochloric acid, acetic acid, maleic acid, p-toluenesulfonic acid, ethanesulfonic acid and the like.

The salts of the compounds within the scope of Formula I can also be in the form of hydrates, for example, mono-, tri-, or polyhydrate.

According to the present invention, optically active, N-substituted 2-hydroxymethylpyrrolidine is readily prepared by treating the corresponding optically active prolinol in an aprotic solvent with two equivalents of n-butyllithium or methyllithium at low temperatures followed by addition of an alkyl halide and recovery of the product by conventional methods. Suitable aprotic solvents include tetrahydrofuran (THF), hexamethylphosphoric triamide, and the like, with THF being preferred. Temperatures may range from about −70° C. to 25° C., with a preferred temperature of about −70° C. Suitable alkyl halides include methyl iodide, ethyl iodide and the like, with methyl iodide being preferred. This method of preparing 1-methylprolinol uses commercially available optically active prolinol or the precursor optically active proline (also commercially available) as a starting material. Commercially available optically active prolines may be reduced directly or via their esters to the corresponding optically active prolinols with lithium aluminum hydride. See Karrer, P., et al. Helv. Chim Acta 31, 1617, 1620–21 (1948).

Alternatively, optically active, N-substituted 2-hydroxymethylpyrrolidine may be prepared from optically active proline by a novel method also developed by the inventors. According to this alternative of the present invention, commercially available, optically active proline is treated with concentrated formic acid and acetic anhydride to provide optically active N-formylproline. The formylproline is then reduced with lithium aluminum hydride in an aprotic solvent (e.g., tetrahydrofuran) to yield the corresponding, optically active 1-methyl-2-hydroxymethylpyrrolidine.

The optically active N-substituted 2-hydroxymethylpyrrolidine is then converted to the corresponding optically active halomethyl hydrochloride by treating a solution of the hydroxymethyl compound in an aprotic solvent with a reagent capable of replacing the hydroxy group by halogen. A preferred aprotic solvent is chloroform although others such as THF may also be used. Reagents capable of replacing the hydroxy group by halogen include thionyl chloride, thionyl bromide, phosphorus oxychloride, and phosphorus tribromide. The preferred reagent is thionyl chloride and the preferred intermediate compound for subsequent further synthesis of optically active nicotine analogs is 1-methyl-2-chloromethylpyrrolidine hydrochloride.

The chloromethyl hydrochloride is then reacted with a nucleophilic cyanide reagent (e.g., an alkali metal cyanide), yielding the corresponding optically active 1-alkyl-2-cyanomethylpyrrolidine. This compound is converted to its anion with lithium diisopropylamide in an aprotic solvent (e.g., THF) at low temperatures (i.e., −70° C.) and condensed with a compound of the formula:

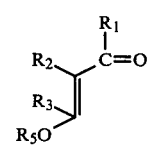

VIII to provide the corresponding optically active intermediate of Formula II.

Ring closure of the intermediate of Formula II is accomplished with 30% hydrogen halide (preferably hydrobromic acid)—acetic acid. Dehalogenation of the resulting compound with hydrogen/palladium chloride and sodium acetate in ethanol affords the desired enantiomerically pure compound of Formula I.

DETAILED DESCRIPTION OF THE INVENTION

The compounds of Formula I are preferably synthesized from commercially-available, enantiomerically pure prolinol or the precursor proline. However, inasmuch as racemic mixtures of the intermediate hydroxymethyl, chloromethyl hydrochloride, and N-substituted cyanomethyl pyrrolidines may be prepared by other methods and methods for resolution of these racemic mixtures are known in the art, the compounds of Formula I may also be synthesized from the recited, resolved intermediates by other processes also within the scope of the present invention. Moreover, nicotine analogs which are not enantiomerically pure may be prepared by the method of this invention. As used herein, compounds of formulae I' and II' correspond to the enantiomerically pure compounds of formulae I and II respectively except that racemic and partially racemic mixtures of the subject compounds are also included within the scope of the I' and II' formulae.

Optically active nicotine analogs are prepared by a novel process which will now be described with particular reference to the preparation of (S)-(−)-5-methylnicotine shown in the following scheme:

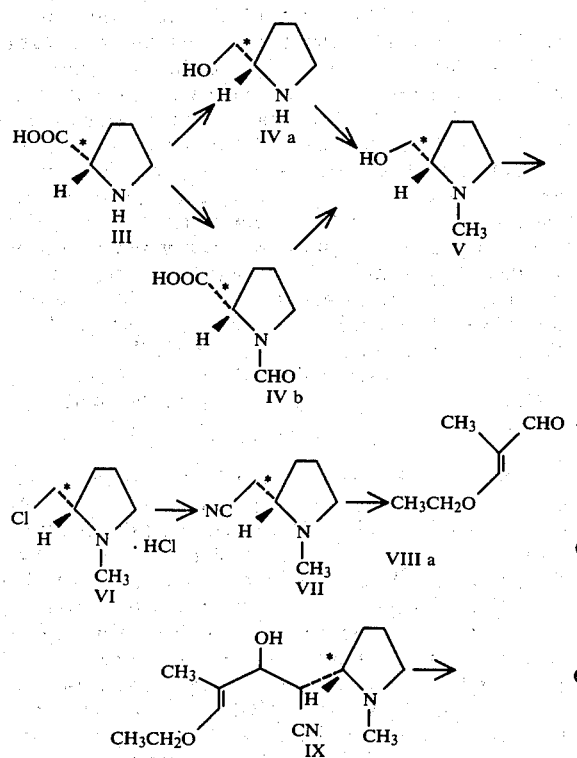

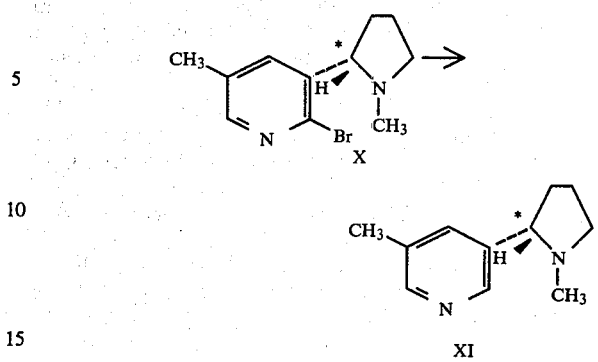

Commercially available L-proline (III) can be reduced to L-prolinol (IV.a.) with lithium aluminum hydride. The L-prolinol (IV.a.) is also commercially available. Treatment of L-prolinol in THF with two equivalents of n-butyllithium at −70° followed by addition of methyl iodide provides (S)-(−)-1-methyl-2-hydroxymethylpyrrolidine (V). Alternatively, formylation of L-proline (III) with formic acid and acetic anhydride produces the N-formylproline (IV.b.) which can be reduced to (S)-(−)-1-methyl-2-hydroxymethylpyrrolidine (V) with lithium aluminum hydride. Compound V is converted to (S)-(−)-1-methyl-2-chloromethylpyrrolidine hydrochloride (VI) with thionyl chloride in chloroform. Reaction of VI with sodium cyanide in ethanol-water affords (S)-(−)-1-methyl-2-cyanomethylpyrrolidine (VII). Compound VII is converted to its anion with lithium diisopropylamide in THF at −70° and condensed with 3-ethoxy-2-methylacrolein VIIIa to provide 5-ethoxy-3-hydroxy-4-methyl-2-(1-methyl-2-pyrrolidinyl)-4-pentenenitrile (IX). Ring closure of IX to (S)-(−)-2-bromo-5-methylnicotine (X) was accomplished with 30% hydrobromic acid-acetic acid. Dehalogenation of X with hydrogen/palladium chloride and sodium acetate in ethanol at 50 psi afforded the desire (S)-(−)-5-methylnicotine (XI). Other nicotinoids may be prepared in analogous fashion by the use of VII and the appropriately substituted acrolein.

Examination of the scheme indicates the brevity of the synthetic procedure—only six steps from commercial L-prolinol (IV). The synthetic procedure is an effective method for producing either optically active or inactive compounds, the activity of the product depending on the nature of the starting material. Enantiomerically pure compounds, i.e., compounds containing at least about 95% and preferably about 100% of one enantiomer, are preferred.

The following examples are illustrative but not limiting of the present invention. Temperatures stated are in degrees Centigrade.

EXAMPLE 1

(S)-(−)-5-Methylnicotine

A. (S)-(−)-1-Methyl-2-hydroxymethylpyrrolidine (V)

(1) To a solution of 5.0 g (0.050 mol) of L-prolinol in 75 ml of dry tetrahydrofuran, under nitrogen, was gradually added 43.5 ml (0.10 mol) of 2.3 M n-butyl lithium in hexane such that the temperature did not rise above −20°. The resultant yellow solution was stirred at −70° for 30 min. followed by the addition of 3.39 ml (7.74 g, 0.055 mol) of methyl iodide over 10 min. The resultant white mixture was stirred at −70° for 5 min. and warmed to room temperature wherein the white precipitate dissolved. The solution was stirred overnight at room temperature and quenched with 10 ml of water. The organic layer was separated and the aqueous layer was extracted with methylene chloride (2×50 ml). The organic layers were combined, dried with magnesium sulfate, and evaporated to provide a mobile, yellow oil. Bulb-to-bulb distillation [oven temp 45°-55° (0.2 torr)] yielded 2.97 g (52%) of the product, a clear, colorless oil: $[\alpha]_D^{20} = -51°$, c=5.35, methanol.

(2) To a solution of 5.0 g (0.0434 mol) of L-proline in 92 ml of 97% formic acid maintained at 5°-10° was slowly added 30 ml of acetic anhydride. The solution was stirred for 2 hr. at room temperature followed by the addition of 35 ml of ice-cold water. Evaporation of the mixture afforded (S)-(−)-N-formylproline ($[\alpha]_D^{2:} = -105°$, c=2.885, methanol), a clear, viscous, pale-yellow oil utilized directly in the next step. The (S)-(−)-N-formylproline was reduced by adding a solution of it in 20 ml of tetrahydrofuran to a slurry of 8.23 g (0.217 mol) of lithium aluminum hydride in 125 ml of tetrahydrofuran under a nitrogen atmosphere. The addition was regulated such that a gentle reflux was maintained. Following addition, the mixture was refluxed for 48 hr. After cooling, the mixture was carefully treated with 8.3 ml of water, followed by 8.3 ml of 15% aq. sodium hydroxide, and finally 25 ml of water. The grey-white mixture was filtered, and the filtrate dried with magnesium sulfate and evaporated to an oil. Bulb to bulb distillation [oven temp 40°-55° (0.15 torr)] afforded 2.823 g of V (57% yield based on L-proline). The optical rotation was identical with that obtained by the synthesis via L-prolinol.

B. (S)-(−)-1-Methyl-2-chloromethylpyrrolidine HCl (VI)

To a solution of 5.99 g (0.052 mol) of (S)-(−)-1-methyl-2-hydroxymethylpyrrolidine in 30 ml of ethanol-free chloroform under nitrogen at 0° was added a solution of 4.75 ml (7.75 g, 0.065 mol) of thionyl chloride in 15 ml of ethanol-free chloroform over 10 min. The resultant clear, brown solution was stirred at room temperature for 30 min. and refluxed for 30 min. After cooling, the dark solution was evaporated to provide a tan-colored, solid residue. The residue was dissolved in absolute ethanol and excess ether was added resulting in the crystallization of a beige-colored solid. The solid was suction-filtered and dried under a nitrogen atmosphere affording 8.02 g (91%): mp 152°-154°; $[\alpha]_D^{20} = -6°$, c=2.35, methanol.

C. (S)-(−)-1-Methyl-2-cyanomethylpyrrolidine (VII)

To a solution of 7.0 g (0.041 mol) of (S)-1-methyl-2-chloromethylpyrrolidine.HCl in 35 ml of 80% aq. ethanol at 0° was added in portions a solution of 3.81 g (0.045 mol) of sodium bicarbonate in 50 ml of water. The mixture was stirred at 0° for 15 min., followed by the addition of a solution of 2.52 g (0.052 mol) of sodium cyanide in 65 ml of 80% aq. ethanol. This mixture was refluxed for 30 min. The resultant solution was cooled, evaporated to a small volume, and extracted with ether (2×25 ml). The combined ethereal layer was dried wtih magnesium sulfate and evaporated to a clear, brown oil. Bulb-to-bulb distillation [oven temp 40°-55° (0.25 torr)] yielded 2.62 g (51%) of the product, a clear, colorless, mobile oil: $[\alpha]_D^{20} = -32.5°$, c=2.57, methanol; picrate, mp 175°-178°.

Anal. Calcd for $C_{13}H_{15}N_5O_7$(picrate): C, 44.19; H, 4.28; N, 19.83. Found: C, 44.00; H, 4.31; N, 19.61.

D. 5-Ethoxy-3-hydroxy-4-methyl-2-(1-methyl-2-pyrrolidinyl)-4-pentenenitrile (IX)

To a solution of 2.54 ml (1.83 g, 0.0181 mol) of diisopropylamine in 50 ml of dry tetrahydrofuran under nitrogen at −20° was added 7.26 ml (0.0167 mol) of 2.3 M n-butyl lithium in hexane such that the temperature did not rise above −10°. After stirring below −20° for 15 min., the solution was cooled to −70°. To the solution of lithium diisopropylamide was added a solution of 1.8 g (0.0145 mol) of (S)-(−)-1-methyl-2-cyanomethylpyrrolidine in 10 ml of dry tetrahydrofuran over 10 min. The residue was washed in with an additional 1 ml of tetrahydrofuran and the resultant white, cloudy mixture stirred for 20 min. at −70°. To this mixture was added a solution of 1.655 g (0.0145 mol) of freshly distilled 3-ethoxy-2-methylacrolein (VIII) in 10 ml of dry tetrahydrofuran over 10 min. The residue was washed in with an additional 1 ml of tetrahydrofuran. The resultant clear, nearly colorless solution was stirred at −70° for 5 min., 0° for 30 min., and room temperature for 2 hr. The yellow solution was quenched with 30 ml of water, and extracted with 50 ml of ether and methylene chloride (2×50 ml). The organic layers were combined, dried with magnesium sulfate and evaporated to a dark yellow, viscous oil. Two bulb-to-bulb distillations [oven temp 115°-130° (0.05 torr)] removed the fore-run of 3-ethoxy-2-methylacrolein and provided 1.94 g (56%) of the product, a viscous, yellow oil; $[\alpha]_D^{20} = -7°$, c=0.56, methylene chloride; EIMS m/e 238 M+, 220 (M+-H$_2$O), 209 (M+-CH$_2$CH$_3$), 84 (1-methylpyrrolidinyl).

E. (S)-(−)-2-Bromo-5-methylnicotine (X)

To a solution of 1.78 g (7.5 mmol) of 5-ethoxy-3-hydroxy-4-methyl-2-(1-methyl-2-pyrrolidinyl)-4-pentenenitrile in 20 ml of glacial acetic acid under nitrogen at 40° was added, dropwise, 40 ml of 30% hydrobromic acid/acetic acid while maintaining the temperature at 40°-45°. The red-brown solution was then heated at 55° for 1 hour. After cooling, the solution was poured into 150 ml of ice-cold water and carefully basified with excess sodium carbonate. The aqueous mixture was extracted with methylene chloride (3×100 ml). The methylene chloride solution was dried with magnesium sulfate and evaporated to 1.215 g (64%) of crude product, a viscous, red-brown oil: $[\alpha]_D^{20} = -22°$, c=0.413, methylene chloride; EIMS m/e 254,256 (M+), 84 (1-methylpyrrolidinyl); picrate, mp 187°-192°.

Anal. Calcd. for $C_{17}H_{18}BrN_5O_7$(picrate): C, 42.16; H, 3.72; N, 14.47. Found: C, 42.64; H, 3.87; N, 14.66.

F. (S)-(−)-5-Methylnicotine (XI)

A mixture of 1.177 g (4.62 mmol) of crude (S)-(−)-2-bromo-5-methylnicotine, 0.327 g (0.4 equiv., 1.85 mmol) of palladium chloride, 1.52 g (4 equiv., 18.5 mmol) of sodium acetate, and 25 ml of absolute ethanol was hydrogenated at 50 psi for 8 hours. The mixture was filtered through celite and evaporated to a small volume which was basified with 15 ml of 10% aq. NaOH. The aqueous mixture was extracted with methylene chloride (3×25 ml). The combined methylene chloride solution was dried with magnesium sulfate and evaporated to a mobile, red-brown oil. Bulb-to-bulb distillation of the oil [oven temp 70°-90° (0.15 torr)] yielded 0.421 g (52%) of the product, a clear, colorless oil: $[\alpha] = -41°$, c=0.504, methylene chloride; EIMS m/e 176 (M+), 84 (1-methylpyrrolidinyl); dipicrate, mp 202°–205°.

Anal. Calcd. for $C_{23}H_{22}N_8O_{14}$(dipicrate): C, 43.53; H, 3.47; N, 17.67. Found: C, 43.27; H, 3.55; N, 17.38.

EXAMPLE NO. 2

(R)-(+)-Nicotine. The preparation of (R)-(+)-nicotine is analogous to that described for (S)-(−)-5-methylnicotine (Example No. 1). The optically active pyrrolidine ring is derived from D-proline and 3-ethoxyacrolein is utilized in the preparation of the pyridine ring.

EXAMPLE NO. 3

(S)-(−)-5-Ethylnicotine. The preparation of (S)-(−)-5-ethylnicotine is analogous to that described for (S)-(−)-5-methylnicotine (Example No. 1). 3-Ethoxy-2-ethylacrolein is utilized in the preparation of the 5-ethylpyridine ring.

EXAMPLE NO. 4

(S)-(−)-6-Methylnicotine. The preparation of (S)-(−)-6-methylnicotine is analogous to that described for (S)-(−)-5-methylnicotine (Example No. 1). 3-Ethoxy-3-methylacrolein is utilized in the preparation of the 6-methylpyridine ring.

EXAMPLE NO. 5

(S)-(−)-5,6-Dimethylnicotine. The preparation of (S)-(−)-5,6-dimethylnicotine is analogous to that described for (S)-(−)-5-methylnicotine (Example No. 1). 3-Ethoxy-2,3-dimethylacrolein is utilized in the preparation of the 5,6-dimethylpyridine ring.

EXAMPLE NO. 6

(S)-(−)-4,5-Dimethylnicotine. The preparation of (S)-(−)-4,5-dimethylnicotine is analogous to that described for (S)-(−)-5-methylnicotine (Example No. 1). 4-Ethoxy-3-methyl-3-buten-2-one is utilized in the preparation of the 4,5-dimethylpyridine ring.

EXAMPLE NO. 7

The candidate compounds were prepared as water solutions at a level of one part of the active ingredient to 5000 parts of water. A nicotine sulfate control was prepared at the commercial level of one part of nicotine to 2500 parts of water. To each preparation, there was added soapy water equivalent to one percent of the final formulation volume. The untreated control consisted of water plus the same amount of soap as added to the candidate compounds and nicotine control. Lily leaves infested with aphids of the genus Myzus were dipped in the prepared solutions until wet (three to five seconds) and then placed in water vials for observation. The results tabulated in the table below were obtained 20 hours following the treatment.

| Compound or Treatment | Dilution | Replicate | % Dead or Moribund | Average |
|---|---|---|---|---|
| (S)-(−)-5-Methylnicotine | 1-5000 | a | 80.6* | |
| | | b | 92.9* | 84.1% |
| | | c | 78.8* | |
| Racemic 5-methylnicotine | 1-5000 | a | 49.7* | |
| | | b | 42.8* | 52.2% |
| | | c | 64.1* | |
| 40% Nicotine Sulfate Control | 1-2500 | a | 98.7 | |
| | | b | 100.0 | 99.6% |
| | | c | 100.0 | |
| Untreated Control | | a | 2.2 | |
| | | b | 3.7 | 3.0% |
| | | c | 3.0 | |

*Mostly young aphids killed.

Optically active 5-methylnicotine showed insecticidal activity quite comparable with the nicotine sulphate control, keeping in mind that the latter solution was twice as concentrated. Racemic 5-methylnicotine gave a lower kill of the aphids, but can still be considered active.

What is claimed is:

1. A process for preparing a compound represented by the formula (I'):

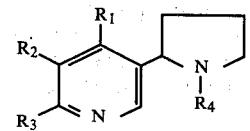

wherein $R_1$ $R_2$, and $R_3$ are hydrogen or a straight chain or branched alkyl group with 1 to 10 carbon atoms and $R_4$ is a straight chain or branched alkyl group with 1 to 10 carbon atoms, which comprises the following steps:

a. treating 1-alkylprolinol in an aprotic solvent with a reagent capable of replacing the hydroxyl group by halogen, said reagent being selected from the group consisting of thionyl chloride, thionyl bromide, phosphorus oxychloride, and phosphorus tribromide, and recovering 1-alkyl-2-halomethylpyrrolidine;

b. treating the product of step (a) with a nucleophilic cyanide reagent to yield 1-alkyl-2-cyanomethylpyrrolidine;

c. converting the product of step (c) to its anion with lithium diisopropylamide in an aprotic solvent at −70° to 25° C. and condensing it with a compound represented by the formula (VIII):

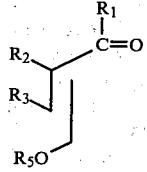

wherein $R_1$, $R_2$, and $R_3$ are as described above and $R_5$ is a straight chain or branched alkyl group with 1 to 10 carbon atoms, yielding a compound represented by the formula II':

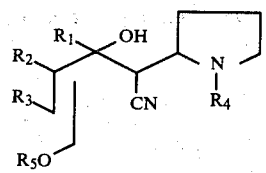

d. closing the ring of the product of step (c) with 30% hydrogen halide-acetic acid at 55° C.; and e. catalytically dehalogenating the product of step (d) with hydrogen/palladium chloride and sodium acetate in ethanol at 50 p.s.i. and isolating the product of said dehalogenation to yield a compound of Formula I'.

2. The method of claim 1 wherein the 1-alkylprolinol is prepared by treating prolinol in an aprotic solvent at temperatures within the range from about −70° to 25° C. with two equivalents of n-butyllithium or methyllithium and then adding alkyl halide to form 1-alkylprolinol.

3. The method of claim 1 wherein the 1-alkylprolinol is 1-methyl prolinol prepared by a method comprising:
   a. treating proline with concentrated formic acid and acetic anhydride and recovering 1-formylproline,
   b. reducing the 1-formylproline with lithium aluminum hydride in the presence of an aprotic solvent, and
   c. recovering 1-methylprolinol.

4. The process of claims 1, 2 or 3 wherein the starting materials, the intermediate products, and the compound represented by the formula (I') are enantiomerically pure.

5. The process of claims 2 or 3 wherein said aprotic solvent is tetrahydrofuran.

6. The process of claim 2 wherein the alkyl halide is alkyl iodide.

7. The process of claim 6 wherein the alkyl iodide is methyl iodide and the product isolated in step e. of claim 1 is a compound represented by the formula I wherein $R_4$=methyl.

8. The method of claim 1 wherein the nucleophilic cyanide reagent comprises an alkali metal cyanide.

9. The method of claim 8 wherein the alkali metal cyanide is sodium cyanide in ethanol-water.

10. The process of claim 1 wherein the anion of the product of step b. is condensed with a compound represented by the formula shown wherein $R_5$ is ethyl.

11. A process for preparing N-alkylprolinols, said alkyl being a straight chain or branched alkyl group with 1 to 10 carbon atoms, wherein the reactions are carried out at temperatures within the range from about −70° to 25° C., which comprises:
   a. treating prolinol in an aprotic solvent with two equivalents of n-butyllithium or methyllithium;
   b. adding an alkyl halide to the mixture resulting from step a., said alkyl being as described above; and
   c. recovering 1-alkylprolinol.

12. The method of claim 11 wherein the aprotic solvent is tetrahydrofuran.

13. The method of claim 11 wherein alkyl iodide is added to the mixture resulting from step a.

14. The method of claim 13 wherein methyl iodide is added to the mixture resulting from step a. and 1-methylprolinol is recovered.

15. The methods of claims 11, 13 or 14 wherein the prolinol treated in step a. is enantiomerically pure and the product is recovered is enantiomerically pure.

16. A process for preparing a compound represented by the formula (I'):

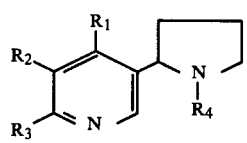

wherein $R_1$, $R_2$, and $R_3$ are hydrogen or a straight chain or branched alkyl group with 1 to 10 carbon atoms and $R_4$ is a straight chain or branched alkyl group with 1 to 10 carbon atoms, which comprises the following steps:
   a. converting 1-alkyl-2-cyanomethylpyrrolidine to its anion with lithium diisopropylamide in an aprotic solvent at −70° to 25° C. and condensing it with a compound represented by the formula (VIII):

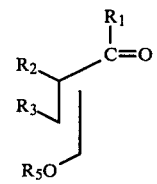

wherein $R_1$, $R_2$, and $R_3$ are as described above and $R_5$ is a straight chain or branched alkyl group with 1 to 10 carbon atoms, yielding a compound represented by the formula (II'):

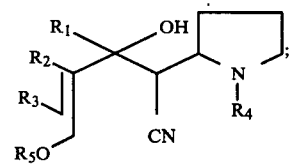

b. closing the ring of the product of step (a) with 30% hydrogen halide-acetic acid at 55° C.; and
   c. catalytically dehalogenating the product of step (b) with hydrogen/palladium chloride and sodium acetate in ethanol at 50 p.s.i. and isolating the product of said dehalogenation to yield a compound of Formula I'.

17. The method of claim 16 wherein the aprotic solvent is tetrahydrofuran.

18. The method of claim 16 wherein the hydrogen halide is hydrobromic acid.

19. The method of claim 16 wherein the 1-alkyl-2-cyanomethylpyrrolidine is enantiomerically pure and the product recovered of Formula I' is enantiomerically pure.

20. The process of claim 16 wherein the anion of 1-alkyl-2-cyanomethylpyrrolidine is condensed with a compound represented by the formula VIII wherein $R_5$ is ethyl.

21. The process of claims 16 or 19 wherein 1-methyl-2-cyanomethylpyrrolidine is converted in step a. and the product isolated in step c. is a compound represented by the formula I' wherein $R_4$ is methyl.

22. A process for preparing a compound represented by the formula (II'):

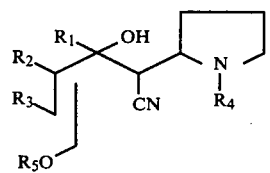

wherein $R_1$, $R_2$, and $R_3$ are hydrogen or a straight chain or branched alkyl group with 1 to 10 carbon atoms and $R_4$ and $R_5$ are a straight chain or branched alkyl group with 1 to 10 carbon atoms, which comprises converting 1-alkyl-2-cyanomethylpyrrolidine to its anion with lithium diisopropylamide in an aprotic solvent at −70° to 25° C. and condensing it with a compound represented by the formula (VIII):

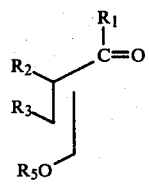

yielding a compound of formula II'.

23. The method of claim 22 wherein the aprotic solvent is tetrahydrofuran.

24. The method of claim 22 wherein the 1-alkyl-2-cyanomethylpyrrolidine and the product of formula II' are enantiomerically pure.

25. The product of claims 22 or 24.

26. The method of claim 1 wherein the aprotic solvent of step a. is chloroform.

27. The method of claim 1 wherein the aprotic solvent of step c. is tetrahydrofuran.

28. The method of claim 1 wherein the reagent capable of replacing the hydroxyl group of 1-alkylprolinol by halogen is thionyl chloride and the product recovered in step a. of claim 1 is 1-alkyl-2-chloromethylpyrrolidine.

* * * * *